United States Patent [19]
Bailey

[11] Patent Number: 5,469,964
[45] Date of Patent: Nov. 28, 1995

[54] MULTIPLE SYRINGE UNSHEATHING AND RESHEATHING DEVICE

[76] Inventor: Eddy R. Bailey, 2115 US Rte. 11, Parish, N.Y. 13131

[21] Appl. No.: 349,043

[22] Filed: Dec. 2, 1994

Related U.S. Application Data

[63] Continuation-in-part of Ser. No. 219,481, Mar. 29, 1994, abandoned.

[51] Int. Cl.⁶ .................................................. B65D 83/10
[52] U.S. Cl. .......................... 206/364; 206/370; 604/192; 604/263; 128/919
[58] Field of Search ..................................... 206/363, 366, 206/365, 364, 370; 128/917, 919; 604/192, 198, 263

[56] References Cited

U.S. PATENT DOCUMENTS

| | | | |
|---|---|---|---|
| 2,617,719 | 11/1952 | Stewart | 23/312 |
| 4,737,149 | 4/1988 | Gillilan | 604/192 |
| 4,738,362 | 4/1988 | Burns et al. | 206/366 |
| 4,801,013 | 1/1989 | Bruno | 206/366 |
| 4,867,309 | 9/1989 | Germain | 206/366 |
| 4,875,583 | 10/1989 | Nosanchuk | 206/365 |
| 4,890,734 | 1/1990 | Gach | 206/366 |
| 4,922,597 | 5/1990 | Ikeda et al. | 29/240 |
| 4,955,865 | 9/1990 | Steiner et al. | 604/192 |
| 4,981,476 | 1/1991 | Aichlmayr et al. | 604/192 |
| 4,986,811 | 1/1991 | Thead et al. | 604/110 |
| 4,989,307 | 2/1991 | Sharpe et al. | 206/366 X |
| 5,007,535 | 4/1991 | Meseke et al. | 206/366 |
| 5,013,299 | 5/1991 | Clark | 604/114 |
| 5,024,666 | 6/1991 | Pituch | 604/263 |
| 5,031,767 | 7/1991 | Bruno | 206/370 |
| 5,067,949 | 11/1991 | Freundlich et al. | 604/263 |
| 5,127,522 | 7/1992 | Ranford | 206/366 |
| 5,287,609 | 2/1994 | Chang | 128/919 X |
| 5,300,028 | 4/1994 | Welcheck | 604/192 X |
| 5,322,164 | 6/1994 | Richardson et al. | 206/366 |

FOREIGN PATENT DOCUMENTS

| | | |
|---|---|---|
| 2586566 | of 1985 | France . |
| 2602340 | of 1987 | France . |
| 2603872 | of 1987 | France . |
| 2601512 | of 1976 | Germany . |
| 2215215 | of 1989 | United Kingdom . |
| WO9000074 | of 1989 | WIPO . |

*Primary Examiner*—Jacob K. Ackun
*Attorney, Agent, or Firm*—St. Onge, Steward, Johnston & Reens

[57] ABSTRACT

A device for unsheathing and resheathing multiple syringe needles is disclosed. The syringe has a needle and a removable sheath covering the needle. The sheath has a predetermined cross sectional dimension. The device has a housing having a plurality of sheath retaining bores and a rotatable shaft extending through the housing. A plurality of paired opposed locking members extend about the shaft and are located so as to straddle a sheath placed into the sheath retaining bore. At least one of the locking members is angled with respect to the other such that the distance therebetween is less than the cross sectional dimension of the sheath at a first position and greater than the cross sectional dimension of the sheath at a second position. Preferably, each locking member is in the shape of an ellipsis. In operation, a sheathed needle is inserted into a sheath retaining bore in the housing and is positioned between opposed locking members. Rotation of the shaft moves the opposed locking members between the first position so as to grip or engage the sheath, and the second position so as to release or disengage the sheath. When the sheath is engaged, a user may apply a force to the syringe and remove the needle from the sheath or reinsert the needle into the sheath.

10 Claims, 2 Drawing Sheets

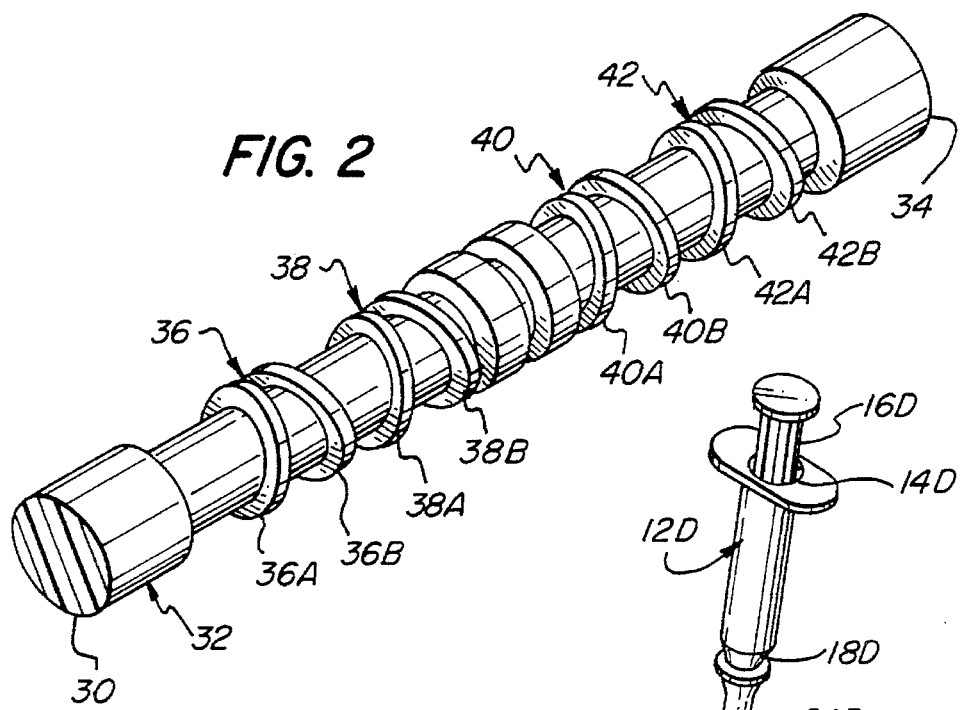
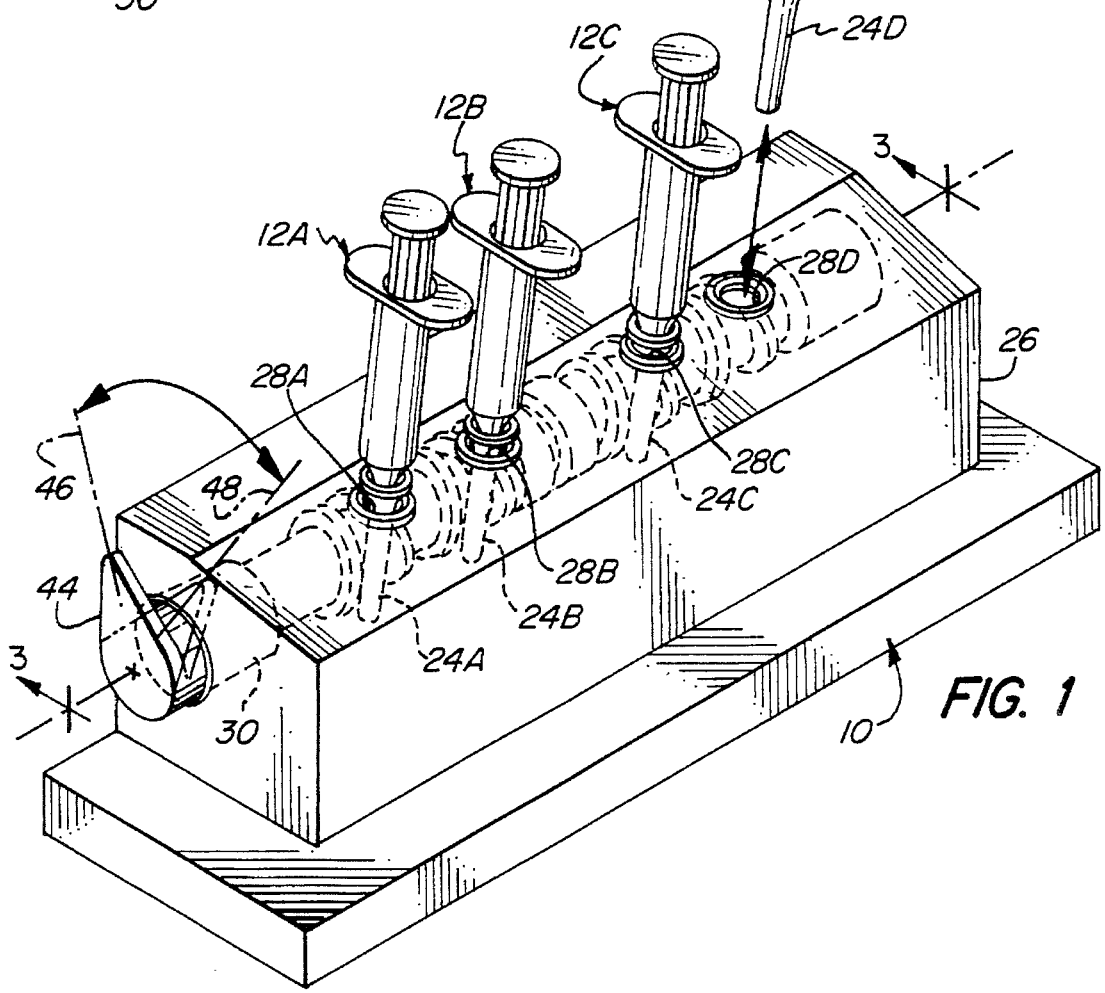

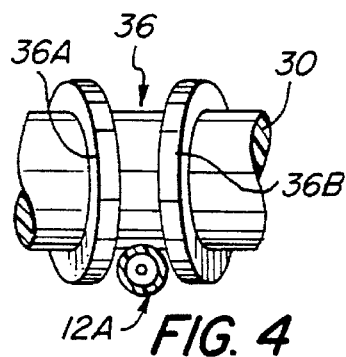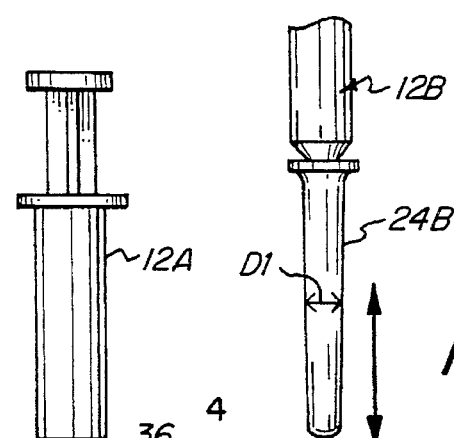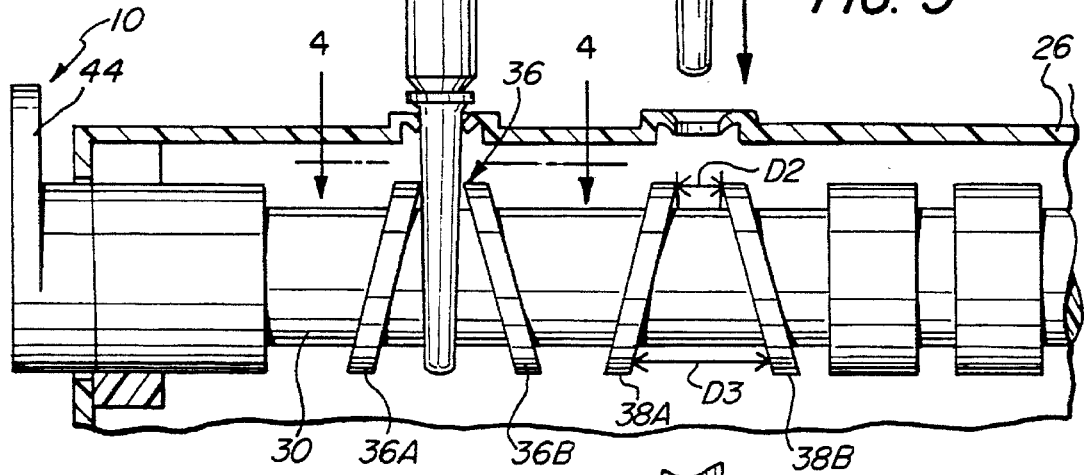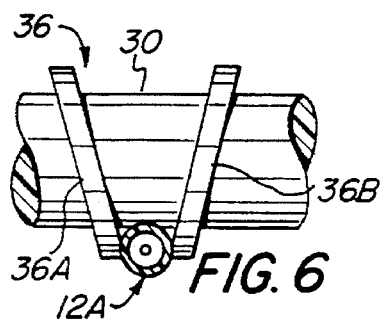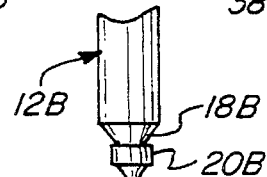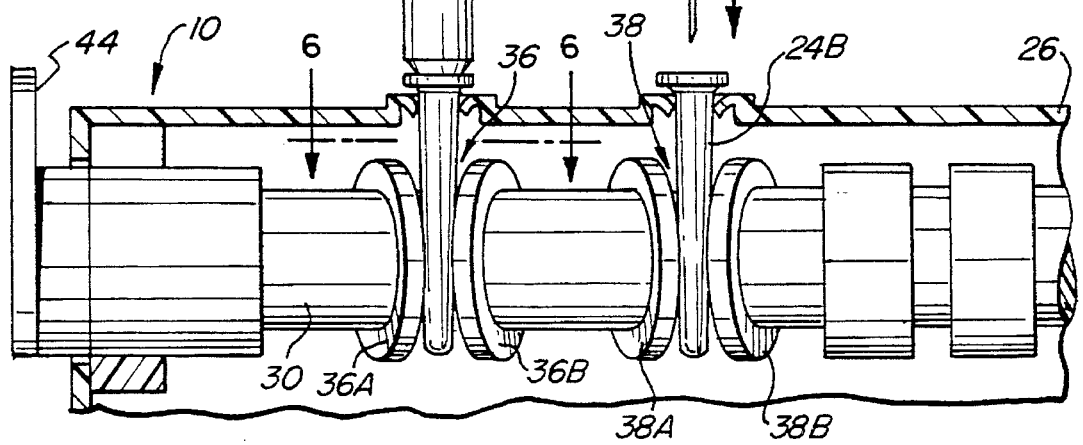

MULTIPLE SYRINGE UNSHEATHING AND RESHEATHING DEVICE

BACKGROUND OF THE INVENTION

This application is a continuation-in-part of an earlier filed application, entitled "Hypodermic Shot Assistant Device", filed Mar. 29, 1994, accorded Ser. No. 08/219,481, now abandoned.

FIELD OF THE INVENTION

The present invention relates to devices for unsheathing and resheathing needles, such as syringe needles.

Needle unsheathing and resheathing devices which assist in preventing accidental needle pricks to health care providers in order to prevent, or reduce, the transmission of communicable diseases are know. For example, U.S. Pat. No. 5,067,949 (the '949 patent) to Freundlich et al. discloses a device for unsheathing, resheathing, and disposing of a single syringe needle. The device comprises an upper member releasably mounted to a disposable container; a vertical passage extends through the upper member and empties through a hole into the container. A sheathed needle can be removably housed in passage. A cam in the upper member pivots to hold the sheathed needle in the passage so that the user may pull the syringe and separate the needle from the sheath, or alternatively, reinsert the needle into the sheath for resheathing.

A device made in accordance with the '949 patent has drawbacks in that it is limited to use with a single syringe. If one desired to carry a plurality of syringes, one would be forced to carry a plurality of individual devices taught by the '949 patent. Further, if one desired to unsheath a plurality of syringes, one would be required to repeat the steps of engaging the cam and separating the needle from the sheath. That is, one would be required to engage the cam member for a first syringe, then separate the first needle from its sheath, engage the cam member for a second syringe, then remove the second needle from its sheath, etc. These two steps (i.e., engaging the cam and separating the needle from its sheath) would be required until the desired number of needles had been unsheathed.

What is desired, therefore, is a needle unsheathing and resheathing device which can house a plurality of sheaths for syringe needles, and which allows one to simultaneously engage or disengage, as desired, all of the sheaths needles for unsheathing or resheathing in one simple and quick step.

SUMMARY OF THE INVENTION

Accordingly, it is an object of the present invention to provide an improved needle unsheathing and resheathing device.

It is another object of the present invention to provide a needle unsheathing and resheathing device which can house a plurality of sheathed needles.

It is still a further object of the present invention to provide a needle unsheathing and resheathing device which can simultaneously grip or release all the sheaths for unsheathing or resheathing, as desired, in one quick and easy step.

To overcome the deficiencies of the prior art and to achieve the objects and advantages listed above, a needle unsheathing and resheathing device is disclosed which comprises: a housing having at least one sheath retaining bore, and preferably, a plurality of sheath retaining bores; a rotatable shaft extending through the housing; and at least one pair of, and preferably a plurality of pairs of, opposed locking members extending at least partially about the shaft and located so as to straddle a sheath placed in the sheath retaining bore.

At least one member of a pair of the locking members is angled with respect to the other such that the distance between the locking members of a pair is less than the cross sectional dimension of the sheath at a first position, and greater than the cross sectional dimension of the sheath at a second position.

In operation, a sheathed needle is inserted into the sheath retaining bore in the housing and is positioned between a pair of opposed locking members. Rotation of the shaft moves the opposed locking members between the first position so as to grip the sheath, and the second position, so as to release the sheath, at the position of the sheathed needle.

When the sheath is gripped or engaged by a pair of locking members, one may apply a force to the syringe so as to remove the needle from the sheath or one may reinsert the needle into the sheath, as desired. When the sheath is released or disengaged from the locking members, the sheath may be freely removed from the device housing.

Advantageously, the device can house a plurality of sheathed syringe needles. Significantly, all of the sheathed needles may be simultaneously engaged for unsheathing or resheathing, as desired, by rotation of a single shaft to a desired position.

The invention and its particular features and advantages will become more apparent from the following detailed description when considered with reference to the accompanying drawings.

BRIEF DESCRIPTION OF THE DRAWINGS

FIG. 1 is an isometric view of a needle unsheathing and resheathing device, constructed in accordance with the present invention, housing a plurality of sheathed needles;

FIG. 2 is an isometric view of a shaft, removed from the device shown in FIG. 1, and a plurality of pairs of locking members extending about the shaft;

FIG. 3 is a cross sectional view taken along line 3—3 of FIG. 1, with portions broken away, showing a sheathed needle released from a pair of locking members;

FIG. 4 is a cross sectional view of a sheathed needle released from a pair of locking members, taken along line 4—4 of FIG. 3;

FIG. 5 is a cross sectional view, with portions broken away, similar to the view shown in FIG. 3, wherein the shaft has been rotated so as to show a sheathed needle gripped by a pair of locking members; and FIG. 6 is a cross sectional view of a sheathed needle gripped by a pair of locking members, taken along line 6—6 of FIG. 5.

DETAILED DESCRIPTION OF THE DRAWINGS

Referring to the drawings in detail, a needle unsheathing and resheathing device is shown and generally designated by the reference numeral 10. It should be noted that for the sake of clarity all the components and parts of device 10 may not be shown and/or marked in all the drawings. As used in this description, the terms "up", "down", "top", "bottom", etc. refer to needle unsheathing and resheathing device 10 when in the orientation illustrated in FIG. 1.

It should also be understood that device 10 has been described for use with syringe needles for the sake of convenience only. Other types of needles, or in fact any like sheathed device (not shown), may be unsheathed and resheathed in the same manner; this description is not limited to syringe needles.

Referring to FIGS. 1, 3, 5, device 10 may house a plurality of syringes 12A, 12B, 12C, 12D which are commonly known. Each syringe 12D, for example, comprises: an elongated hollow chamber 14D, a plunger 16D slidably received in chamber 14D, and a tip 18D extending distally from chamber 14D. Hub 20B, best shown in FIG. 5, is attached to tip 18B, and needle 22B extends distally from hub 20B. Cap or sheath 24B, 24D is releasably attached to hub 20B, 20D at a distal portion of the syringe 12B, 12D, respectively, in order to receive and cover the syringe needle 22B, for example.

Removable sheath or cap 24A, 24B, 24C, 24D, for example, has a predetermined cross sectional dimension, such as a diameter, D1, which is measured at substantially the point of contact of locking members 36, 38, 40, 42, discussed below. See FIG. 3. D1 is generally about ⅛ inch to about ¼ inch inch.

Needle sheath clamping or gripping device 10 comprises a housing 26 having at least one sheath retaining bore, such as 28A, and preferably a plurality of sheath retaining bores 28B, 28C, 28D. See FIG. 1. Device 10 may be made of any suitable material, such as plastic, and may be made by any suitable method, such as injection molding.

As shown in FIGS. 1, 3, 5, a rotatable shaft 30 extends through housing 26. Referring to FIG. 2, shaft 30 comprises a first end 32 and a second end 34, and at least one pair 36 of opposed locking members 36A, 36B extend at least partially about shaft 30 between ends 32, 34. Most preferably, a plurality of pairs 36, 38, 40, 42 of opposed locking members extend at least partially about shaft 30. Handle 44 (FIGS. 1, 3, 5) is attached by any suitable method (such as gluing) to one end, for example 32 (FIG. 2), of the shaft 30, for rotatably driving the shaft 30.

Each pair of locking members 36, 38, 40, 42 (FIG. 2) corresponds to a sheath retaining bore 28A, 28B, 28C, 28D (FIG. 1) in housing 26. More particularly, locking members 36A, 36B straddle sheath 24A placed in bore 28A (best shown in FIGS. 3–6); locking members 38A, 38B straddle sheath 24B placed in bore 28B; locking members 40A, 40B straddle sheath 24C placed in bore 28C; and locking members 42A, 42B straddle sheath 24D placed in bore 28Do Preferably, each pair of locking members 36, 38, 40, 42 comprises a pair of opposed locking members, each member of each pair having the shape of a partial ellipsis (not shown) which extends at least partially about shaft 30. Each locking member having the shape of a partial ellipsis is positioned so as to grip needle sheath 24A, for example, when inserted into bore 28A, for example. Most preferably, each member of each pair of opposed locking members 36, 38, 40, 42 has the shape of an ellipsis which extends completely about shaft 30.

Referring to FIGS. 3, 5, at least one locking member of a pair of locking members, for instance member 38A of pair 38, is angled toward the other, for instance member 38B, such that the distance between members 38A and 38B decreases from greater than the cross sectional dimension D1 of sheath 24B to slightly less than the cross sectional D1 of sheath 24B. Thus, rotation of shaft 30 causes the distance between locking members 38A and 38B to change relative to the position of a sheath 24B. In this way, a sheathed syringe 12B can be inserted through bore 28B (FIG. 1) and between locking members 38A and 38B when members 38A and 38B are farther apart than dimensional distance D1, and clamped by locking members 38A and 38B when shaft 30 is rotated such that the dimensional distance between locking members 38A and 38B is less than D1 of shaft 30.

Referring to FIG. 3, the distance D2 at the closest point of each pair of locking members, such as 38A and 38B, is slightly less than the cross sectional dimension D1 of the sheath 24B. This distance D2 is sufficient to cause locking members 38A, 38B to grip the needle sheath 24B when in the clamped or engaged position with sufficient pressure to permit syringe 12B to be withdrawn from device 10 while sheath 24B remains therein. Needle 22B can also be reinserted into sheath 24B when sheath 24B is clamped by locking members 38A, 38B. Preferably, distance D2 is about ¹⁄₁₆ inch to about ³⁄₁₆ inch.

Conversely, the distance D3 at the point of greatest separation of each member of each pair of locking members, 38A and 38B, for example, is sufficiently large so that sheath 24B is released or disengaged by the locking members 38A, 38B when sheath 24B is in the released position. When in the released position, sheath 24B may be freely removed from device 10. In the preferred embodiment, D3 is about ½ inch to about ⅝ inch.

In operation, a sheathed needle is inserted into a sheath retaining bore, such as 28D (FIG. 1) in the housing 26 and is positioned between opposed locking members 42A, 42B, for example. Rotation of the shaft 30 between position shown by line 46 (FIG. 1) to the position shown by line 48 moves the opposed locking members 38A, 38B between the released or disengaged position (shown in FIGS. 1, 3, 4) to the gripped or engaged position (shown in FIGS. 5, 6) so as to clamp the sheath 24B at the position of the sheathed needle 12B.

Advantageously, device 10 can house a plurality of sheathed syringe needles 12A, 12B, 12C, 12D. Because all of the pairs 36, 38, 40, 42 of the locking members can be simultaneously moved from the engaged or disengaged position relative to a sheathed needle inserted into a corresponding bore 28A, 28B, 28C, 28D by rotation of a single shaft 30, all of the sheathed needles 12A, 12B, 12C, 12D may be simultaneously engaged for unsheathing or resheathing. This allows the operator to prepare quickly for administering a plurality of injections, and, more importantly, requires only one of the operator's hands, freeing the other hand for other tasks, such as restraining a patient.

The present invention, therefore, provides a new and useful apparatus and method for unsheathing and resheathing needles, such as syringes.

It should be understood that device 10 has been shown with four pairs of locking members 36, 38, 40, 42, but as many locking members as desired may be used, requiring modifications to the shaft 30 and housing 26 which will be obvious to one skilled in the art after reading this disclosure.

It should be understood that the foregoing is illustrative and not limiting and that obvious modifications may be made by those skilled in the art without departing from the spirit of the invention. Accordingly, reference should be made primarily to the accompanying claims, rather than the foregoing specification, to determine the scope of the invention.

What is claimed is:

1. A needle sheath gripping device for use with a syringe having a needle and a removable sheath covering the needle, the sheath having a predetermined cross sectional dimension, the device comprising:

a housing having at least one sheath retaining bore for removably housing a sheath; and a rotatable shaft extending through the housing, the shaft comprising a first end and a second end, and at least one pair of opposed locking members extending at least partially about the shaft and located so as to straddle a sheath placed in the sheath retaining bore, at least one of the locking members being angled with respect to the other such that the distance therebetween is less than the cross sectional dimension of the sheath at a first rotational position and greater than the cross sectional dimension of the sheath at a second rotational position, wherein when a sheath is inserted into the bore in the housing and is positioned between a pair of opposed locking members, rotation of the shaft moves the opposed locking members between the first position and second position so as to either grip or release the sheath.

2. The needle sheath gripping device of claim 1, the device further comprising a plurality of pairs of opposed locking members, each locking member extending at least partially about the shaft.

3. The needle sheath gripping device of claim 2, wherein each pair of locking members comprises a pair of opposed locking members having the shape of partial ellipses, each ellipsis-shaped member extending at least partially about the shaft.

4. The needle sheath gripping device of claim 2, wherein each pair of locking members comprises a pair of locking members having the shape of an ellipses, each ellipses-shaped member extending about the shaft.

5. The needle sheath gripping device of claim 1, further comprising a handle, attached to one end of the shaft, for rotatably driving the shaft.

6. An apparatus for gripping and releasing a sheath during unsheathing and resheathing of a needle, the needle having a removable sheath, the sheath having a predetermined cross sectional dimension, the apparatus comprising:

a housing having a sheath retaining bore; and a rotatable shaft extending through the housing, the shaft comprising a first end and a second end, and a plurality of paired opposed locking members extending about the shaft, at least one of the locking members being angled with respect to the other such that the distance therebetween is less than the cross sectional dimension of the sheath at a first position and greater than the cross sectional dimension of the sheath at a second position, wherein when a sheath is inserted into the sheath retaining bore and is positioned between opposed locking members, rotation of the shaft moves the opposed locking members between the first and second position so as to either grip or release the sheath.

7. The apparatus of claim 6, wherein each locking member comprises a locking member having a partial ellipsis shape, wherein each ellipsis shaped member extends at least partially about the shaft.

8. The apparatus of claim 6, the device further comprising a handle attached to one end of the shaft for rotatably driving the shaft.

9. A method for unsheathing or resheathing a syringe, the syringe having a needle and a removable sheath covering the needle, the sheath having a predetermined cross sectional dimension, the method comprising the following steps:

providing a housing having a plurality of sheath retaining bores, and a shaft extending through the housing, the shaft comprising a first end and a second end, and a plurality of paired opposed locking members extending at least partially about the shaft between the two ends, at least one of the locking members being angled with respect to the other such that the distance therebetween is less than the cross sectional dimension of the sheath at a first position and greater than the cross sectional dimension of the sheath at a second position;

inserting a sheath into the sheath retaining bore in the housing and between opposed locking members of a pair; and rotating the shaft such that rotation of the shaft moves the opposed locking members between the first and second position so as to either grip or release the sheath.

10. The method of claim 9, further comprising the step of attaching a handle to one end of the shaft for rotatably driving the shaft.

* * * * *